US005731487A

United States Patent [19]

Tamura et al.

[11] Patent Number: 5,731,487
[45] Date of Patent: Mar. 24, 1998

[54] PROCESS FOR PRODUCING OLEFIN HAVING A TERMINAL DOUBLE BOND

[75] Inventors: Mitsuhisa Tamura; Kenshi Uchida; Yoshiaki Ito; Kiyoshi Iwanaga, all of Ichihara, Japan

[73] Assignee: Sumitomo Chemical Company, Limited, Osaka, Japan

[21] Appl. No.: 694,836

[22] Filed: Aug. 9, 1996

Related U.S. Application Data

[63] Continuation of Ser. No. 571,030, Dec. 12, 1995, abandoned, which is a continuation of Ser. No. 208,861, Mar. 11, 1994, abandoned.

[30] Foreign Application Priority Data

| Mar. 12, 1993 | [JP] | Japan | 5-052026 |
| Nov. 4, 1993 | [JP] | Japan | 5-275369 |

[51] Int. Cl.$^6$ .................................................. C07C 2/24
[52] U.S. Cl. .................. 585/513; 585/510; 585/511; 585/512; 585/520; 585/521; 585/522; 585/523; 585/527; 585/530
[58] Field of Search .................................. 585/510, 511, 585/512, 513, 520, 521, 522, 523, 527, 530

[56] References Cited

U.S. PATENT DOCUMENTS

| 3,726,939 | 4/1973 | Zuech . | |
| 4,668,838 | 5/1987 | Briggs | 585/513 |
| 4,853,356 | 8/1989 | Briggs | 502/117 |
| 5,376,612 | 12/1994 | Reagan et al. | 502/104 |
| 5,491,272 | 2/1996 | Tanaka et al. | 585/520 |

FOREIGN PATENT DOCUMENTS

| 0416304A2 | 8/1990 | European Pat. Off. . |
| 0537609A2 | 7/1992 | European Pat. Off. . |
| 0608447 | 8/1994 | European Pat. Off. . |
| 0611743 | 8/1994 | European Pat. Off. . |

| 9300350 | 1/1993 | South Africa . |
| 2271116 | 4/1994 | United Kingdom . |

*Primary Examiner*—Elizabeth D. Wood
*Attorney, Agent, or Firm*—Sughrue, Mion, Zinn, Macpeak & Seas, PLLC

[57] ABSTRACT

The present invention provides a process for producing olefin having a terminal double bond by trimerizing at least one monomer selected from a group consisting of ethylene, propylene, and 1-butene, which comprises using a catalyst comprising a product prepared from
(1) component (A): a chromium compound represented by the formula [1]

$$CrX_mY_n \qquad [1]$$

wherein X represents carboxylic acid residue, 1,3-diketone residue, halogen atom or alkoxyl group, Y represents amine, phosphine, phosphine oxide, nitrosyl group or ether, m means an integer of from 2 to 4 and n means an integer of from 0 to 4, component (B): a heterocyclic compound having a pyrrole ring unit or an imidazole ring unit, and component (C): an aluminum compound represented by the formula [2]

$$AlR_kZ_{3-k} \qquad [2]$$

wherein R represents hydrogen atom or alkyl group having 1 to 10 carbon atoms, Z represents halogen atom and k means a real number of from 0 to 3, or (2) component (A) and component (B'): a heterocyclic compound having a pyrrole ring unit or an imidazole ring unit and further containing a bond between aluminum and nitrogen in the pyrrole ring or the imidazole ring. According to the present invention, olefin having a terminal double bond such as 1-hexene can be obtained effectively and conveniently, and the process is also good in the industrial application.

17 Claims, No Drawings

PROCESS FOR PRODUCING OLEFIN HAVING A TERMINAL DOUBLE BOND

This is a Continuation of application Ser. No. 08/571,030 filed Dec. 12, 1995, now abandoned, which is a Continuation of application Ser. No. 08/208,861 filed Mar. 11, 1994, now abandoned.

FIELD OF THE INVENTION

The present invention relates to a process for producing olefins having a terminal double bond by trimerizing at least one monomer selected from a group consisting of ethylene, propylene and 1-butene.

BACKGROUND OF THE INVENTION

For producing olefins having a terminal double bond, such as 1-hexene, by trimerizing an olefin monomer, such as ethylene, the following processes are known: (a) a process which comprises using a catalyst comprising the reaction product of a chromium compound, a hydrocarbyl aluminum hydrolyzed with a certain amount of water, and a donor ligand (U.S. Pat. No. 4,668,838); (b) a process which comprises using a catalyst comprising a chromium containing compound such as chromium pyrrolides, and an aluminum compound (European Unexamined Patent Publication No. 0 416 304); (c) a process which comprises using a catalyst comprising a chromium complex containing a coordinating polydentate ligand, and an aluminoxane (European Unexamined Patent Publication No. 0 537 609).

However, the process (a) has problems of insufficient activity of the catalyst and poor selectivity to the intended product. It also has difficulty of maintaining the activity of the catalyst. The process (b) has problems with insufficient activity of the catalyst and is difficult in preparation of the catalyst. The process (c) has problem of poor selectivity to the intended product by the catalyst. Therefore, none of these processes have reached a satisfactory level in producing said olefin.

SUMMARY OF THE INVENTION

An object of the present invention is to provide a convenient and effective process for producing olefins having a terminal double bond such as 1-hexene, which is also good in industrial application.

This and other objects will become apparent from the following description of the invention.

In the process for producing olefins having a terminal double bond by trimerizing olefin monomer, the present inventors have found that application of a specific catalyst in the present invention to the reaction can satisfy the object described above based not only on its high activity and high selectivity to the intended product but also on its convenient preparation and easy preservation.

The present invention provides a process for producing olefins having a terminal double bond by trimerizing at least one monomer selected from a group consisting of ethylene, propylene and 1-butene, which comprises using a catalyst comprising a product prepared from:

(1) component (A): a chromium compound represented by the formula [1]

$$CrX_mY_n \qquad [1]$$

wherein X represents carboxylic acid residue, 1,3-diketone residue, halogen atom or alkoxyl group; Y represents amine, phosphine, phosphine oxide, nitrosyl group or ether; m means an integer of from 2 to 4; and n means an integer of from 0 to 4, component (B): a heterocyclic compound having a pyrrole ring unit or an imidazole ring unit, and component (C): an aluminum compound represented by the formula [2]

$$AlR_kZ_{3-k} \qquad [2]$$

wherein R represents hydrogen atom or alkyl group having 1 to 10 carbon atoms; Z represents halogen atom; and k means a real number of from 0 to 3, or (2) component (A) and component (B'): a heterocyclic compound having a pyrrole ring unit or an imidazole ring unit and further containing a bond between aluminum and nitrogen in the pyrrole ring or the imidazole ring.

DETAILED DESCRIPTION

The details of the present invention will be described below.

Examples of the olefin having a terminal double bond in the present invention (hereinafter referred to as "terminal olefin") are 1-hexene, nonenes, dodecenes, and the like. Preparation of 1-hexene from ethylene is especially important because of its industrial significance.

The catalyst to be used in the present invention is a catalyst comprising a product prepared from components (A), (B) and (C), or components (A) and (B') which are respectively defined below.

Component (A) is a chromium compound represented by the formula [1]

$$CrX_mY_n \qquad [1]$$

wherein X represents carboxylic acid residue, 1,3-diketone residue, halogen atom or alkoxyl group; Y represents amine, phosphine, phosphine oxide, nitrosyl group or ether; m means an integer of from 2 to 4; and n means an integer of from 0 to 4.

As the carboxylic acid residues in the chromium compound [1], those having 1 to 20 carbon atoms are preferred. Examples of the carboxylic acid residue are the residues of alkanoic acids such as 2-ethylhexanoic acid, acetic acid, butyric acid, neopentanoic acid, lauric acid and stearic acid; oxyalkanoic acid such as oxy-2-ethylhexanoic acid; haloalkanoic acid such as dichloroethylhexanoic acid; acylalkanoic acid such as acetoacetic acid; dicarboxylic acid such as oxalic acid; and cycloalkanoic or cycloalkylalkanoic acid such as naphthenic acid. 2-Ethylhexanoic acid and naphthenic acid are more preferred.

As the 1,3-diketone residues in the chromium compound [1], those having 5 to 20 carbon atoms are preferred. Examples of the 1,3-diketone residue are the residues of aliphatic 1,3-diketone such as acetylacetone, 2,2,6,6-tetramethyl-3,5-heptanedione and 1,1,1-trifluoroacetylacetone; and aryl 1,3-diketone such as benzoylacetone.

As the halogen atom in the chromium compound [1], chlorine atom, bromine atom, iodine atom and fluorine atom are preferred. Chlorine atom is more preferred.

As the alkoxyl group in the chromium compound [1], those having 1 to 20 carbon atoms are preferred. Examples of the alkoxyl group are tert.-butoxyl group and isopropoxyl group.

Examples of the amine in the chromium compound [1] are pyridines such as pyridine, 4-methylpyridine, 4-ethylpyridine, 4-propylpyridine, 4-isopropylpyridine, 4-tert.-butylpyridine, 4-phenylpyridine, 3,4-diphenylpyridine, 3,4-dimethylpyridine; arylamines such as aniline; and cyclic amines such as 1,4,7-trimethyl- 1,4,7-triazacyclononane. Pyridine, 4-ethylpyridine, 4-isopropylpyridine and 4-phenylpyridine are preferred.

Examples of the phosphine in the chromium compound [1] are trialkylphosphines such as tributylphosphine, and triarylphosphines such as triphenylphosphine.

Examples of the phosphine oxide in the chromium compound [1] are trialkylphosphine oxides such as tributylphosphine oxide, and triarylphosphine oxides such as triphenylphosphine oxide.

Examples of the ether in the chromium compound [1] are tetrahydrofuran, and the like.

Specific examples of the chromium compound [1] (component (A)) include chromium(III) tris(2-ethylhexanoate), chromium(II) bis(2-ethylhexanoate), chromium(III) tris(naphthenate), chromium(II) bis (naphthenate), chromium(III) tris(acetate), chromium(II) bis (acetate), chromium(III) tris(acetylacetonate), chromium (III) tris(2,2,6,6-tetramethyl-3,5-heptanedionate), chromium (II) bis(acetylacetonate), chromium(III) tris (trifluoroacetylacetonate), chromium(III) tribenzoylacetonate, chromium(IV) tetra(t-butoxide), trichlorotrianiline chromium(III), trichlorotripyridine chromium(III), trichlorotritetrahydrofuran chromium(III), trichlorotri(4-ethylpyridine) chromium(III), trichlorotri(4-isopropylpyridine) chromium(III), trichlorotri(4-phenylpyridine) chromium(III), dichlorobispyridine chromium(II), dichlorodinitrosyl bis(triphenylphosphine oxide) chromium(II), dichlorobis(triphenylphosphine oxide) chromium(II), dichlorodinitrosyl bis(4-ethylpyridine) chromium(II), dichloro bis(4-ethylpyridine) chromium(II), trichloro bis(tributylphosphine) chromium(III) dimer, trichloro(1,4,7-trimethyl-1,4,7-triazacyclononane) chromium(III), and the like. Chromium(III) tris(2-ethylhexanoate), chromium(II) bis(2-ethylhexanoate), chromium(III) tris(naphthenate), chromium(II) bis (naphthenate), chromium(IV) tetra(t-butoxide), trichlorotripyridine chromium(III), trichlorotri(4-ethylpyridine) chromium(III), trichlorotri(4-isopropylpyridine) chromium (III), trichlorotri(4-phenylpyridine) chromium(III), and trichlorotritetrahydrofuran chromium(III) are preferred.

Component (B) is a heterocyclic compound having a pyrrole ring unit or an imidazole ring unit. The heterocyclic compound having a pyrrole ring unit is preferred. In the case that the heterocyclic compound further contains a bond between aluminum and nitrogen in the pyrrole ring or the imidazole ring which may be called component (B'), component (C) is not essential and may be omitted from the catalyst. The heterocyclic compound having a pyrrole ring unit containing nitrogen-aluminum bond is more preferred.

Examples of the heterocyclic compound (component (B)) include pyrroles such as pyrrole, 2,5-dimethylpyrrole, 2,5-diethylpyrrole, 2,5-dipropylpyrrole, 2-methylpyrrole, 2-ethylpyrrole, 3-methylpyrrole, 3-ethylpyrrole, 3-propylpyrrole, 3-butylpyrrole, 3-heptylpyrrole, 3-octylpyrrole, 3-ethyl-2,4-dimethylpyrrole, 2,3,4,5-tetramethylpyrrole, and 4,5,6,7-tetrahydroindole; indoles such as indole; carbazoles such as carbazole; and imidazoles such as imidazole, 2-methylimidazole, 2-ethylimidazole, 2-isopropylimidazole, and 4-methylimidazole; and the like. Preferred examples are pyrrole, 2,5-dimethylpyrrole, 3-heptylpyrrole and 3-octylpyrrole.

Examples of the heterocyclic compound further containing a bond between aluminum and nitrogen in the pyrrole ring unit or the imidazole ring unit (component (B')) include alkylaluminum pyrrolides such as diisobutyl aluminum-2, 5-dimethylpyrrolide, diethyl aluminum-2,5-dimethylpyrrolide, dimethyl aluminum-2,5-dimethylpyrrolide, diisobutylaluminum pyrrolide, diethylaluminum pyrrolide, dimethylaluminum pyrrolide; and alkylaluminum imidazolides such as diisobutylaluminum imidazolide, diethylaluminum imidazolide, and dimethylaluminum imidazolide; and the like. Preferred examples thereof include diisobutyl aluminum-2,5-dimethylpyrrolide, diethyl aluminum-2,5-dimethylpyrrolide, dimethyl aluminum-2,5-dimethylpyrrolide, diisobutylaluminum pyrrolide, diethylaluminum pyrrolide and dimethylaluminum pyrrolide. Diisobutyl aluminum-2,5-dimethylpyrrolide, diethyl aluminum-2,5-dimethylpyrrolide, diisobutylaluminum pyrrolide and diethylaluminum pyrrolide are more preferred.

The heterocyclic compound further containing a bond between aluminum and nitrogen in the pyrrole ring unit or the imidazole ring unit (component (B')) can be synthesized by known methods.

The known methods may be, for example, a process of mixing the heterocyclic compound having the pyrrole ring unit or the imidazole unit containing a bond between hydrogen and nitrogen and component (C). Alternatively, the methods include steps of converting the heterocyclic compound having a pyrrole ring unit or the imidazole unit containing a bond between hydrogen and nitrogen to its metal salt, and reacting the metal salt with an aluminum halide represented by the formula [3]

$$AlR'_{k'}Z'_{3-k'} \quad [3]$$

wherein R' represents hydrogen atom or alkyl group having 1 to 10 carbon atoms; Z' represents halogen atom; and k' means a real number larger than 0 and smaller than 3. The halogen atom may be chlorine atom, bromine atom, iodine atom, or fluorine atom.

Examples of the aluminum halide [3] include diisobutylaluminum chloride, diethylaluminum chloride, isobutylaluminum dichloride, ethylaluminum dichloride, ethylaluminum sesquichloride, and the like.

Conversion of the heterocyclic compound having the pyrrole ring or the imidazole unit containing a bond between hydrogen and nitrogen to its metal salt can be carried out by, for example, a process of reacting the compound with an alkali metal, an alkaline earth metal, or a derivative thereof. Examples of these metals or derivatives include lithium, methyllithium, butyllithium, phenyllithium, sodium, sodium hydride, potassium, potassium hydride, methylmagnesium bromide, methyl magnesium iodide, ethylmagnesium bromide, propylmagnesium bromide, butylmagnesium chloride, and the like.

Component (C) is an aluminum compound represented by the formula [2]

$$AlR_kZ_{3-k} \quad [2]$$

wherein R represents hydrogen atom or alkyl group having 1 to 10 carbon atoms; Z represents halogen atom; and k means a real number of from 0 to 3. k is usually at a range of from 1 to 3.

Examples of the aluminum compound (component (C)) include trialkylaluminum such as triisobutylaluminum, tricyclohexylaluminum, tri-n-hexylaluminum, tri-n-octylaluminum, triethylaluminum, trimethylaluminum; alkylaluminum hydride such as diisobutylaluminum hydride; alkylaluminum halide such as diethylaluminum chloride, ethylaluminum sesquichloride, ethylaluminum dichloride. Trialkylaluminum and alkylaluminum hydride are preferred. Triethylaluminum, triisobutylaluminum and diisobutylaluminum hydride are more preferred.

Preferred catalysts in the present invention includes those which comprise a product prepared from components (A), (B') and (C), wherein X in the formula [1] of the chromium compound as component (A) is halogen atom and Y in the same formula is amines or ethers, more preferably pyridines or tetrahydrofuran; component (B') has a pyrrole ring unit; and component (C) is trialkylaluminum.

Specific examples of the preferred catalyst are those which comprise a product prepared from trichlorotripyridine chromium(III), trichlorotri(4-ethylpyridine) chromium(III), trichlorotri(4-isopropylpyridine) chromium(III), trichlorotri (4-phenylpyridine) chromium(III) or trichlorotritetrahydrofuran chromium as component (A), diisobutylaluminum 2,5-dimethylpyrrolide as component (B), and triethylaluminum as component (C).

The amount of the heterocyclic compound (component (B) or (B')) is usually 1 to 100 moles, preferably 2 to 30 moles per 1 mole of the chromium compound (component (A)). The amount of the aluminum compound (component (C)) is usually 1 to 100 moles, preferably 2 to 30 moles per 1 mole of the chromium compound(component (A)).

The catalyst may further be prepared from water, alcohol, phenol or its derivative as component (D), in addition to components (A), (B) and (C), or components (A) and (B'). That is, the catalyst may be prepared from components (A), (B), (C) and (D), or alternatively, from components (A), (B') and (D).

The preferred alcohol is that having 1 to 10 carbon atoms. Examples of the alcohol are methanol, ethanol, and hexafluoroisopropanol. The preferred phenol or its derivative is that having 6 to 20 carbon atoms. Examples thereof are phenol, hydroquinone, resorcinol, bisphenol A, N,N-dimethyl-m-aminophenol, 3,4,5-trimethoxyphenol, 3,5-dimethoxyphenol, p-methoxyphenol, 2,4,6-tri-t-butylphenol, 4,4'-biphenol, 1,1'-bi-2-naphthol, 2,4,6-trichlorophenol, and catechol. Hydroquinone, resorcinol, bisphenol A, N,N-dimethyl m-aminophenol, 3,4,5-trimethoxyphenol, 3,5-dimethoxyphenol, p-methoxyphenol, and 2,4,6-tri-t-butylphenol are more preferred.

The amount of the component (D) is usually 0.1 to 100 moles, preferably 0.5 to 30 moles per 1 mol of the chromium compound (component (A)).

The catalyst may further be prepared from acid or ester as component (E), in addition to components (A), (B) and (C), or components (A) and (B'). That is, the catalyst may be prepared from components (A), (B), (C) and (E), or alternatively, from components (A), (B') and (E).

Examples of the acid or ester include sulfonic acids such as methanesulfonic acid, trifluoromethanesulfonic acid, and camphorsulfonic acid; carboxylic acids such as trifluoroacetic acid; acid anhydrides such as trifluoromethanesulfonic anhydride; inorganic acids such as sulfuric acid, hydrochloric acid, nitric acid, and phosphoric acid, polyphosphoric acid; and esters such as trimethylsilyl trifluoromethanesulfonate and dimethyl sulfate. Trifluoromethanesulfonic acid, trimethylsilyl trifluoromethanesulfonate, sulfuric acid, and phosphoric acid are preferred.

The amount of the component (E) is usually 0.1 to 100 moles, preferably 0.5 to 30 moles per 1 mole of chromium compound (component (A)).

The catalyst may further be prepared from diene as component (F), in addition to components (A), (B) and (C), or components (A) and (B'). That is, the catalyst may be prepared from components (A), (B), (C) and (F), or alternatively, from components (A), (B') and (F).

Examples of the diene include 1,3-butadiene, isoprene, 1,4-pentadiene, 1,3-pentadiene, 2,3-dimethyl-1,3-butadiene, 1,5-hexadiene, 1,4-hexadiene, 1,3-hexadiene, 2,4-hexadiene, 1,6-heptadiene, norbornadiene, 1,4-diphenyl-1, 3-butadiene, 1,3-cyclohexadiene, and 1,5-cyclooctadiene. Isoprene, 1,3-butadiene, 1,3-pentadiene, and 1,6-heptadiene are preferred.

The amount of the component (F) is usually 0.1 to 100 moles, preferably 0.5 to 30 moles per 1 mole of chromium compound (component (A)).

The catalyst may be prepared by, for example, dissolving components (A), (B) and (C) in a hydrocarbon or halogenated hydrocarbon solvent with stirring in an atmosphere of an inert gas such as argon and nitrogen. Examples of the hydrocarbon or halogenated hydrocarbon solvent are butane, isobutane, pentane, hexane, heptane, 1-hexene, 1-octene, toluene, xylene, chlorobenzene, and dichlorobenzene.

The trimerization reaction of the present invention can be carried out by, for example, a process of adding at least one monomer selected from the group consisting of ethylene, propylene and 1-butene to the catalyst and the solvent in an autoclave, and then heating the mixture for the reaction.

The amount of the catalyst may be determined to adjust the concentration of the chromium atom in the reaction solution usually in the range of 0.000001 to 0.05 mol/l, preferably 0.00001 to 0.01 mol/l.

The reaction temperature is usually in the range of 20° to 200° C., preferably 20° to 150° C.

The reaction pressure is usually at the range from atmospheric pressure to 200 kg/cm$^2$, preferably 10 to 100 kg/cm$^2$. The reaction time is usually from 0.1 to 8 hours, preferably from 0.5 to 7 hours. The target terminal olefin can be separated and recovered from the reaction mixture, for example, by distillation.

The catalyst in the present invention may be carried on inorganic carriers such as silica, alumina, silica-alumina, zeolite and aluminum phosphate, or on organic carriers such as ion-exchange resins, polystyrene and polyvinylpyridine.

The reaction in the present invention can be carried out by supplying hydrogen to the reaction system so as to prevent string-like adhesive polymers from being formed. The amount of hydrogen to be provided is determined to adjust the ratio of hydrogen in the hydrogen and at least one monomer selected from the group consisting of ethylene, propylene and 1-butene usually in the range of 0.1 to .50 mol %, preferably 1 to 25 mol %.

According to the present invention, olefin having a terminal double bond such as 1-hexene can be obtained effectively and conveniently by using the catalyst in the present invention based not only on its high activity and high selectivity to the intended product but also on its convenient preparation and easy preservation.

EXAMPLE

The following examples illustrate the present invention in more detail. However, the present invention is not limited to such examples.

Example 1

Heptane solvent which had been previously deaerated and dehydrated under argon atmosphere was cooled down in an icy cold water bath. A catalyst was prepared by dissolving (A1): trichlorotri(4-isopropylpyridine) chromium(III) 13 mg (0.025 mmol), (B1): diisobutylaluminum 2,5- dimethylpyrrolide 12 mg (0.051 mmol: 0.092 mol/l heptane solution), and (C1): triethylaluminum 21 mg (0.18 mmol: 1.0 mol/l heptane solution) in the cooled heptane solvent with stirring. The heptane solution of the catalyst was poured into an autoclave having an inner volume of 0.2 l, and then ethylene was provided into the autoclave up to the inner pressure of 25 kg/cm$^2$G. The reaction system in the autoclave was then heated under stirring for the trimerization reaction. The reaction temperature, the reaction pressure, and the reaction time were respectively set at to 100° C., 40 kg/cm$^2$G, and 2 hours. Ethylene was provided into the reactor to maintain the pressure during the reaction. After the reaction, the reaction mixture was separated by solid-liquid separation. The amount of polymers produced was determined by weighing the amount of the solid. The amount of 1-hexene was determined by analyzing the liquid phase with gas chromatography. The reaction conditions and results are shown in Tables 1 and 2. Preparation of (B1): diisobutylaluminum-2,5-dimethylpyrrolide Heptane solvent 15 ml which had been previously deaerated and dehydrated under an argon atmosphere was cooled down in an icy cold water bath. n-Butyllithium 102 mg (1.6 mmol:1.6 mol/l hexane solution) and 2,5-dimethylpyrrole 152 mg (1.6 mmol) were added to the cooled heptane solvent and sufficiently stirred in an icy cold water bath for 15 minutes and at 25° C. for 30 minutes. The mixed solution was again cooled down in an icy cold water bath, then diisobutylaluminum chloride 283 mg (1.6 mmol:a 1.0 mol/l heptane solution) was added dropwise to the cooled solution. The solution with diisobutylaluminum chloride was sufficiently stirred in an icy cold water bath for 15 minutes and at 25° C. for 1 hour. Settling and cooling down the thus stirred solution in an icy cold water bath gave a heptane solution of diisobutylaluminum-2,5-dimethylpyrrolide as a supernatant liquid.

Examples 2 to 26 and Comparative Examples 1 and 2

The procedures of Examples 2 to 26 and Comparative Examples 1 and 2 were carried out in the same manner as in Example 1 except that the reaction conditions were varied as shown in Tables 1 to 4. The results are shown in Table 1 to 4.

TABLE 1

| No. | 1 | 2 | 3 | 4 | 5 | 6 | 7 |
|---|---|---|---|---|---|---|---|
| Type of Component*1 | | | | | | | |
| (A) | A1 | A2 | A3 | A4 | A5 | A6 | A6 |
| (B) | B1 | B1 | B1 | B1 | B1 | B1 | B1 |
| (C) | C1 | C1 | C1 | C1 | C1 | C1 | C1 |
| (D) | — | — | — | — | — | — | — |
| (E) | — | — | — | — | — | — | — |
| (F) | — | — | — | — | — | — | — |
| Molar Ratio*2 | | | | | | | |
| (A) | 1 | 1 | 1 | 1 | 1 | 1 | 1 |
| (B) | 2 | 2 | 2 | 2 | 2 | 6 | 6 |
| (C) | 7 | 7 | 7 | 7 | 7 | 5 | 5 |
| (D) | 0 | 0 | 0 | 0 | 0 | 0 | 0 |
| (E) | 0 | 0 | 0 | 0 | 0 | 0 | 0 |
| (F) | 0 | 0 | 0 | 0 | 0 | 0 | 0 |
| Amount of Catalyst*3 | 0.46 | 0.46 | 0.46 | 0.46 | 0.46 | 0.82 | 0.84 |
| Reaction Temperature (°C.) | 100 | 100 | 100 | 100 | 100 | 100 | 50 |
| Reaction Pressure (kg/cm$^2$G) | 40 | 40 | 40 | 40 | 40 | 45 | 40 |
| Reaction Time (hr) | 2 | 2 | 2 | 2 | 2 | 2 | 2 |
| Results | | | | | | | |
| Activity (g/g-Cr)*4 | 30526 | 30356 | 26118 | 23272 | 22298 | 7854 | 8696 |
| Selectivity*5 | | | | | | | |
| 1-Hexene | 80 | 74 | 75 | 77 | 76 | 76 | 45 |
| Polymer | 2 | 2 | 1 | 2 | 2 | 1 | 13 |

TABLE 2

| No. | 8 | 9 | 10 | 11 | 12 | 13 | 14 |
|---|---|---|---|---|---|---|---|
| Type of Component*1 | | | | | | | |
| (A) | A6 | A6 | A2 | A3 | A6 | A6 | A6 |
| (B) | B1 | B2 | B3 | B3 | B3 | B3 | B3 |
| (C) | — | C1 | C1 | C1 | C1 | C1 | C1 |
| (D) | — | — | — | — | — | — | — |
| (E) | — | — | — | — | — | — | — |
| (F) | — | — | — | — | — | — | — |
| Molar Ratio*2 | | | | | | | |
| (A) | 1 | 1 | 1 | 1 | 1 | 1 | 1 |
| (B) | 51 | 6 | 4 | 4 | 6 | 7 | 6 |
| (C) | 0 | 11 | 11 | 11 | 11 | 11 | 11 |
| (D) | 0 | 0 | 0 | 0 | 0 | 0 | 0 |
| (E) | 0 | 0 | 0 | 0 | 0 | 0 | 0 |
| (F) | 0 | 0 | 0 | 0 | 0 | 0 | 0 |
| Amount of Catalyst*3 | 0.29 | 1.6 | 0.64 | 1.6 | 1.6 | 1.6 | 1.6 |
| Reaction Temperature (°C.) | 100 | 80 | 80 | 80 | 80 | 80 | 80 |
| Reaction Pressure (kg/cm$^2$G) | 40 | 40 | 40 | 40 | 40 | 40 | 30 |
| Reaction Time (hr) | 2 | 2 | 2 | 2 | 2 | 6 | 2 |
| Results | | | | | | | |
| Activity (g/g-Cr)*4 | 3308 | 2718 | 1418 | 1416 | 2128 | 3882 | 1458 |
| Selectivity (%)*5 | | | | | | | |
| 1-Hexene | 78 | 87 | 81 | 75 | 78 | 68 | 80 |
| Polymer | 4 | 1 | 2 | 1 | 2 | 4 | 2 |

TABLE 3

| No. | 15 | 16 | 17 | 18 | 19 | 20 | 21 |
|---|---|---|---|---|---|---|---|
| Type of Component*1 | | | | | | | |
| (A) | A6 | A6 | A6 | A6 | A6 | A6 | A6 |
| (B) | B3 | B3 | B3 | B3 | B3 | B3 | B3 |
| (C) | C2 | C1 | C1 | C1 | C1 | C1 | C1 |
| (D) | — | — | — | — | — | D1 | D2 |
| (E) | — | — | — | — | — | — | — |
| (F) | — | — | — | — | — | — | — |
| Molar Ratio*2 | | | | | | | |
| (A) | 1 | 1 | 1 | 1 | 1 | 1 | 1 |
| (B) | 6 | 6 | 6 | 11 | 7 | 4 | 4 |
| (C) | 14 | 11 | 11 | 20 | 14 | 11 | 11 |
| (D) | 0 | 0 | 0 | 0 | 0 | 1.5 | 1.5 |
| (E) | 0 | 0 | 0 | 0 | 0 | 0 | 0 |
| (F) | 0 | 0 | 0 | 0 | 0 | 0 | 0 |
| Amount of Catalyst*3 | 1.6 | 1.6 | 1.6 | 1.6 | 1.6 | 0.64 | 0.64 |
| Reaction Temperature (°C.) | 80 | 70 | 90 | 80 | 80 | 80 | 80 |
| Reaction Pressure (kg/cm²G) | 20 | 40 | 40 | 20 | 20 | 40 | 40 |
| Reaction Time (hr) | 2 | 2 | 2 | 2 | 2 | 2 | 2 |
| Results | | | | | | | |
| Activity (g/g-Cr)*4 | 1514 | 1502 | 1962 | 1420 | 840 | 1810 | 2674 |
| Selectivity (%)*5 | | | | | | | |
| 1-Hexene | 65 | 76 | 71 | 56 | 75 | 63 | 60 |
| Polymer | 3 | 2 | 4 | 2 | 1 | 5 | 3 |

TABLE 4

| | Examples | | | | | Comparative Examples | |
|---|---|---|---|---|---|---|---|
| No. | 22 | 23 | 24 | 25 | 26 | 1 | 2 |
| Type of Component*1 | | | | | | | |
| (A) | A6 | A6 | A6 | A6 | A6 | — | — |
| (B) | B3 | B3 | B3 | B3 | B3 | — | — |
| (C) | C1 | C1 | C1 | C1 | C1 | — | C1 |
| (D) | D3 | D4 | — | — | — | — | — |
| (E) | — | — | E1 | E2 | — | — | — |
| (F) | — | — | — | — | F1 | — | — |
| (X) | — | — | — | — | — | X1 | — |
| (Y) | — | — | — | — | — | Y1 | — |
| (Z) | — | — | — | — | — | — | Z1 |
| Molar Ratio*2 | | | | | | | |
| (A) | 1 | 1 | 1 | 1 | 1 | 1 | 0 |
| (B) | 4 | 4 | 4 | 4 | 7 | 0 | 0 |
| (C) | 11 | 11 | 11 | 11 | 11 | 0 | 33 |
| (D) | 3 | 3 | 0 | 0 | 0 | 0 | 0 |
| (E) | 0 | 0 | 2 | 3 | 0 | 0 | 0 |
| (F) | 0 | 0 | 0 | 0 | 1 | 0 | 0 |
| (X) | 0 | 0 | 0 | 0 | 0 | 34 | 0 |
| (Y) | 0 | 0 | 0 | 0 | 0 | 63 | 0 |
| (Z) | 0 | 0 | 0 | 0 | 0 | 0 | 1 |
| Amount of Catalyst*3 | 0.64 | 0.64 | 0.64 | 0.64 | 1.6 | 1.5 | 0.67 |
| Reaction Temperature (°C.) | 80 | 80 | 80 | 80 | 80 | 80 | 80 |
| Reaction Pressure (kg/cm²G) | 40 | 40 | 40 | 40 | 40 | 20 | 20 |
| Reaction Time (hr) | 2 | 2 | 2 | 2 | 2 | 2 | 2 |
| Results | | | | | | | |
| Activity (g/g-Cr)*4 | 1900 | 1164 | 2244 | 1032 | 1434 | 784 | 644 |
| Selectivity (%)*5 | | | | | | | |
| 1-Hexene | 71 | 75 | 65 | 88 | 72 | 77 | 45 |
| Polymer | 5 | 3 | 2 | 5 | 1 | 21 | 17 |

Notes
*1Type of Component
A1: Trichlorotri(4-isopropylpyridine) chromium(III)
A2: Trichlorotripyridine chromium(III)
A3: Trichlorotri(tetrahydrofuran) chromium(III)
A4: Trichlorotri(4-phenylpyridine) chromium(III)
A5: Trichlorotri(4-ethylpyridine) chromium(III)
A6: Chromium(III) tris(2-ethylhexanoate)
B1: Diisobutylaluminum-2,5-dimethylpyrrolide
B2: 3-Octylpyrrole
B3: Pyrrole
C1: Triethylaluminum
C2: Triisobutylaluminum
C3: Diisobutylaluminum hydride
D1: Water
D2: Hydroquinone
D3: Hexafluoroisopropanol
D4: Methanol
E1: Sulfuric Acid
E2: Trimethylsilyl trifluoromethanesulfonate
F1: Isoprene
X1: 1,2-Dimethoxyethane
Y1: Poly(isobutyl aluminum oxide)
Z1: Cr(C$_4$H$_4$N)$_3$Na(1,2-dimethoxyethane)$_3$Cl
*2Molar Ratio of the Components to the component (A)
*3Amount of the Catalyst: Concentration of the chromium atom in the reaction solution (mmol/l)
*4Activity: Total amount (gram) of products (1-hexene, polymer, and others) per 1 gram of the chromium atom in the catalyst
*5Selectivity
Selectivity of 1-Hexene: (Amount (gram) of 1-hexene produced/Total amount (gram) of products) × 100
Selectivity of Polymer: (Amount (gram) of polymers produced/Total amount (gram) of products) × 100

What is claimed is:

1. A process for producing olefins having a terminal double bond which comprises the steps of:

preparing a catalyst by dissolving
component (A): a chromium compound represented by the formula $$CrX_m$$

wherein X represents a carboxylic acid residue, a halogen atom or an alkoxyl group; and m means an integer of from 2 to 4;

component (B): a heterocyclic compound having a pyrrole ring unit or an imidazole ring unit, and component (C): an aluminum compound represented by the formula $$AlR_kZ_{3-k}$$

wherein R represents a hydrogen atom or an alkyl group having 1 to 6 carbon atoms; Z represents a halogen atom; and k means a real number of from 0 to 3, in a hydrocarbon or halogenated hydrocarbon, and trimerizing at least one monomer selected from the group consisting of ethylene, propylene and 1-butene by contacting said monomer with said catalyst under effective trimerization conditions;

wherein said catalyst is only dissolved in said hydrocarbon or halogenated hydrocarbon selected from the group consisting of butane, pentane, hexane, heptane, chlorobenzene and dichlorobenzene in an atmosphere of inert gas prior to said trimerization.

2. A process for producing olefins having a terminal double bond which comprises the steps of:

preparing a catalyst by dissolving component (A): a chromium compound represented by the formula CrXm wherein X represents a carboxylic acid residue, a halogen atom or an alkoxyl group; and m means an integer of from 2 to 4; and component (B'): a heterocyclic compound having a pyrrole ring unit or an imidazole ring unit and further containing a bond between aluminum and nitrogen in the pyrrole ring or the imidazole ring, in a hydrocarbon or halogenated hydrocarbon, and trimerizing at least one monomer selected from the group consisting of ethylene, propylene and 1-butene by contacting said monomer with said catalyst under effective trimerization conditions;

wherein said catalyst is only dissolved in said hydrocarbon or halogenated hydrocarbon selected from the group consisting of butane, pentane, hexane, heptane, chlorobenzene and dichlorobenzene in an atmosphere of inert gas prior to said trimerization.

3. A process according to claim 2, wherein the step of preparing a catalyst includes the step of adding component (D): water, alcohol, phenol or its derivative, to components (A) and (B').

4. A process according to claim 2, wherein the step of preparing a catalyst includes the step of adding component (E): acid or ester, to components (A) and (B)'.

5. A process according to claim 2, wherein the step of preparing a catalyst includes the step of adding component (F): diene, to components (A) and (B').

6. A process according to claim 2, wherein the step of trimerizing at least one monomer includes the step of selecting ethylene as said at least one monomer.

7. A process according to claim 1, wherein the step of preparing a catalyst includes the step of adding component (D): water, alcohol, phenol or its derivative, to components (A), (B) and (C).

8. A process according to claim 1, wherein the step of preparing a catalyst includes the step of adding component (E): acid or ester, to components (A), (B) and (C).

9. A process according to claim 1, wherein the step of preparing a catalyst includes the step of adding component (F): diene, to components (A), (B) and (C).

10. A process according to claim 1, wherein the step of trimerizing at least one monomer includes the step of selecting ethylene as said at least one monomer.

11. A process according to claim 1, wherein the step of preparing a catalyst includes the step of selecting a heterocyclic compound having a pyrrole ring unit as component (B).

12. A process according to claim 2, wherein the step of preparing a catalyst includes the step of selecting a heterocyclic compound having a pyrrole ring unit as component (B').

13. A process according to claim 1, wherein the step of preparing a catalyst includes the step of selecting trialkylaluminum or dialkylaluminum hydride as component (C).

14. A process according to claim 2, wherein the step of preparing a catalyst includes the step of adding component (C): an aluminum compound represented by the formula $$AlR_kZ_{3-k}$$

wherein R represents hydrogen atom or alkyl group having 1 to 10 carbon atoms; Z represents halogen atom; and k means a real number of from 0 to 3, to components (A) and (B').

15. A process according to claim 14, wherein the step of preparing a catalyst includes the step of selecting component (A) wherein X represents halogen atom and Y represents amine and/or ether as component (A), a heterocyclic compound having a pyrrole ring unit and further containing a bond between aluminum and nitrogen in the pyrrole ring as component (B'), and trialkylaluminum as component (C).

16. A process according to claim 15, wherein the step of preparing a catalyst includes the step of selecting component (A) wherein Y is pyridines or tetrahydrofuran.

17. A process according to claim 16, wherein the step of preparing a catalyst includes the step of selecting trichlorotripyridine chromium (III), trichlorotri(4-ethylpyridine) chromium (III), trichlorotri(4-isopropylpyridine)chromium (III), trichlorotri(4-phenylpyridine)chromium (III) or trichlorotri(tetrahydrofuran)chromium (III) as component (A), diisobutylammonium 2,5-dimethylpyrrolide as component (B'), and triethylaluminum as component (C).

* * * * *